(12) United States Patent
Shelton et al.

(10) Patent No.: US 11,931,578 B2
(45) Date of Patent: Mar. 19, 2024

(54) ACOUSTIC SENSING FOR RESPIRATION DETECTION

(71) Applicant: THE ALFRED E. MANN FOUNDATION FOR SCIENTIFIC RESEARCH, Valencia, CA (US)

(72) Inventors: Brian M. Shelton, Altadena, CA (US); Sahar Elyahoodayan, Los Angeles, CA (US); Harshit R. Suri, Pasadena, CA (US)

(73) Assignee: THE ALFRED E. MANN FOUNDATION FOR SCIENTIFIC RESEARCH, Valencia, CA (US)

(*) Notice: Subject to any disclaimer, the term of this patent is extended or adjusted under 35 U.S.C. 154(b) by 0 days.

(21) Appl. No.: 17/228,593

(22) Filed: Apr. 12, 2021

(65) Prior Publication Data

US 2021/0316139 A1    Oct. 14, 2021

Related U.S. Application Data

(60) Provisional application No. 63/008,118, filed on Apr. 10, 2020.

(51) Int. Cl.
*A61N 1/36* (2006.01)
*A61B 7/00* (2006.01)
(Continued)

(52) U.S. Cl.
CPC ............ *A61N 1/3611* (2013.01); *A61B 7/003* (2013.01); *A61N 1/05* (2013.01); *A61N 1/37217* (2013.01); *A61N 1/3787* (2013.01)

(58) Field of Classification Search
CPC .... A61N 1/3611; A61N 1/05; A61N 1/36135; A61N 1/3601; A61N 1/36125; A61N 1/36078; A61N 1/0548
See application file for complete search history.

(56) References Cited

U.S. PATENT DOCUMENTS

2005/0039745 A1* 2/2005 Stahmann ............ A61B 5/0809
                                                128/204.18
2012/0253249 A1* 10/2012 Wilson ................. A61N 1/3611
                                                607/42
(Continued)

FOREIGN PATENT DOCUMENTS

WO   2017083754 A1   5/2017
WO   2017184753 A1   10/2017

OTHER PUBLICATIONS

Kohli et al.; Prototype development of an electrical impedance based simultaneous respiratory and cardiac monitoring system for gated radiotherapy. Biomed Eng Online. Oct. 14, 2014;13:144. doi: 10.1186/1475-925X-13-144. PMID: 25316509; PMCID (Year: 2014).*

(Continued)

*Primary Examiner* — Paula J Stice
(74) *Attorney, Agent, or Firm* — ARENTFOX SCHIFF LLP

(57) ABSTRACT

The disclosure provides systems and methods for treating obstructive sleep apnea using an acoustic sensor configured to detect acoustic sounds generated by the heart and lungs. Sensory data from the acoustic sensor is used by an implanted stimulation system to determine when to deliver electrical stimulation to a nerve which innervates an upper airway muscle, such as the hypoglossal nerve, to treat sleep apnea.

26 Claims, 10 Drawing Sheets

(51) Int. Cl.
*A61N 1/05* (2006.01)
*A61N 1/372* (2006.01)
*A61N 1/378* (2006.01)

(56) References Cited

U.S. PATENT DOCUMENTS

| | | | |
|---|---|---|---|
| 2013/0060150 A1* | 3/2013 | Song | A61B 7/003 600/529 |
| 2014/0194793 A1 | 7/2014 | Nakata et al. | |
| 2015/0039045 A1* | 2/2015 | Ni | A61N 1/36139 607/42 |
| 2015/0224307 A1* | 8/2015 | Bolea | A61N 1/3611 607/42 |
| 2017/0001016 A1* | 1/2017 | De Ridder | A61N 1/36082 |
| 2017/0245945 A1* | 8/2017 | Zuhars | A61B 90/39 |

OTHER PUBLICATIONS

Person. (2013). Transthoracic impedance measurements in patient monitoring. Transthoracic Impedance Measurements in Patient Monitoring | Analog Devices. Retrieved Jul. 25, 2022, from https://www.analog.com/en/technical-articles/transthoracic-impedance-measurements-in-patient-monitoring.html (Year: 2013).*

International Search Report and Written Opinion issued by International Searching Authority in corresponding International Application No. PCT/US2021/026916, dated Jul. 19, 2021.

Azadeh Yadollahi et al., "Acoustic Obstructive sleep apnea detection", Proceedings of the 31st Annual International Conference of the IEEE Engineering in Medicine and Biology Society: Engineering the Future of Biomedicine, EMBC 2009, IEEE, Sep. 3, 2009, pp. 7110-7113.

Yu Fang et al., "A Novel Sleep Respiratory Rate Detection Method for Obstructive Sleep Apnea Based on Characteristic Moment Waveform", Journal of Healthcare Engineering, vol. 2018, Jan. 1, 2018, pp. 1-10.

* cited by examiner

ACOUSTIC SENSING FOR RESPIRATION DETECTION

CROSS-REFERENCE TO RELATED APPLICATION

This application claims the benefit of U.S. Provisional Application Ser. No. 63/008,118, entitled "ACOUSTIC SENSING FOR RESPIRATION DETECTION" and filed on Apr. 10, 2020, which is expressly incorporated by reference herein in its entirety.

BACKGROUND

Obstructive Sleep Apnea (OSA) is a sleep disorder involving obstruction of the upper airway during sleep. The obstruction of the upper airway may be caused by the collapse of or increase in the resistance of the pharyngeal airway, often resulting from tongue obstruction. The obstruction of the upper airway may be caused by reduced genioglossus muscle activity during the deeper states of NREM sleep. Obstruction of the upper airway may cause breathing to pause during sleep. Cessation of breathing may cause a decrease in the blood oxygen saturation level, which may eventually be corrected when the person wakes up and resumes breathing. The long-term effects of OSA include high blood pressure, heart failure, strokes, diabetes, headaches, and general daytime sleepiness and memory loss, among other symptoms.

OSA is extremely common, and may have a prevalence similar to diabetes or asthma. Over 100 million people worldwide suffer from OSA, with about 25% of those people being treated. Continuous Positive Airway Pressure (CPAP) is a conventional therapy for people who suffer from OSA. More than five million patients own a CPAP machine in North America, but many do not comply with use of these machines because they cover the mouth and nose and, hence, are cumbersome and uncomfortable.

Neurostimulators may be used to open the upper airway as a treatment for alleviating apneic events. Such therapy may involve stimulating the nerve fascicles of the hypoglossal nerve (HGN) that innervate the intrinsic and extrinsic muscles of the tongue in a manner that prevents refraction of the tongue which would otherwise close the upper airway during the inspiration period of the respiratory cycle. ImThera Medical is currently in FDA clinical trials for a stimulator system that is used to stimulate the trunk of the HGN with a nerve cuff electrode. The stimulation system does not provide a sensor or sensing, and therefore, the stimulation delivered to the HGN trunk is not synchronized to the respiratory cycle. Thus, the tongue and other muscles that are innervated by nerve fascicles of the HGN trunk are stimulated irrespective of the respiratory cycle.

The rationale for this treatment method appears to be that it is enough simply to tone the tongue muscle and other nearby muscles, so that the tongue muscle does not retract in a manner that would cause OSA. The belief is that it is not necessary to specifically target the protraction (i.e., anterior movement) of the tongue muscle and to synchronize the occurrence of tongue protraction when it is most needed, i.e., during inspiration. The nerve cuff electrode of the ImThera Medical system has multiple electrode contacts helically surrounding the proximal part of the HGN nerve trunk. So, instead, each electrode contact delivers stimulation in a sequential order to the HGN trunk. For example, if a three-electrode contact nerve cuff is used, electrode contact #1 stimulates, then stops, electrode contact #2 stimulates, then stops, electrode contact #3 stimulates, then stops, then electrode contact #1 stimulates, then stops and so on. Since all or most electrode contacts deliver stimulation, there is no selection process to choose the best one or two electrode contacts that is finally used to deliver the best stimulation to alleviate sleep apnea.

A disadvantage of the ImThera Medical system is that it does not target tongue protraction coincident with the inspiration phase of respiration, since it does not have a sensor to enable synchronized stimulation of the respiratory cycle. Since there is no attempt to synchronize the stimulation with the respiratory cycle, the tongue protraction does not occur when it would appear to help the most—during inspiration when OSA can occur. Also, because the HGN trunk contains nerve fascicles that innervate muscles other than the muscle that extend the tongue, the Imthera Medical method of stimulation at the HGN trunk does not just target the specific protrusor muscles of the tongue muscle, but other muscles that are not targeted. Thus, stimulating the HGN trunk in an arbitrary manner may recruit other nerve fascicles of the HGN trunk that may not contribute to the protraction of the tongue.

Another company, Inspire Medical Systems, Inc., does offer a stimulation system with a sensor, and therefore does attempt to time the onset of stimulation to the breathing cycle. This system, which is FDA approved for sale in the United States since April 2010, uses a simple, bipolar electrode (two electrode contacts only) within a nerve cuff electrode and implants the electrode at the branch of the HGN that is responsible for protruding the tongue. A simple, two-electrode contact or three-electrode contact cuff electrode can be used at the branch nerve, unlike the HGN trunk, because at the distal branch location, the nerve fascicles generally innervate the specific tongue protrusor muscle and not other muscles.

However, implanting the electrode at a branch of the HGN requires additional surgery time, which increases trauma to the patient and increases the substantial expense of operating room time. By attaching the nerve cuff electrode to the proximal section of the main trunk of the HGN, compared to placing the nerve cuff electrode at the more distal end of the HGN, the surgical time may be reduced by approximately one hour or more. Further, because the branch nerve is small and more difficult to isolate than the HGN trunk, implanting a nerve cuff electrode at the branch site demands heightened expertise from the otolaryngologist/Ear Nose and Throat (ENT) surgeon or neurosurgeon, which may increase the chance for error and surgical risks. Furthermore, because the distal location of the HGN has a smaller diameter of nerves, and hence the required electrodes need to be smaller, the smaller nerve cuff electrode may be more difficult to manufacture.

Thus, it is certainly desirable to implant the nerve cuff electrode at the trunk of the hypoglossal nerve. However, one must then deal with the fact that the target nerve fascicles may be near the center of the nerve trunk and are not easily isolated and stimulated, while at the same time avoiding stimulating other non-targeted fascicles in the same nerve trunk.

A pressure sensor is connected to neurostimulator of the Inspire system by a lead, thereby allowing the pressure sensor to be placed remotely from the implanted site of the neurostimulator. However, the fact that the pressure sensor has a lead connected to the stimulator necessitates some additional surgery, because the sensor lead is another appendage that must be implanted.

As illustrated by the foregoing summary, current systems for treating OSA either use pressure sensors near the diaphragm to detect the start of inspiration or use no inspiration detection at all. Furthermore, the use of a pressure sensor that is distal to an implantable pulse generator (IPG) requires a longer surgery. Thus, there remains a need for improved systems and methods for selectively recruiting only the fascicles of the hypoglossal nerve in synchronization with the respiratory cycle for treating OSA of a patient, while minimizing the surgery time and effort required to implant the neurostimulation components in the patient. There exists a further needs for systems and methods which can provide increased accuracy with respect to the detection of a subject's respiratory cycle and leverage this increased accuracy to better treat subjects suffering from OSA.

BRIEF SUMMARY OF EXEMPLARY ASPECTS OF THE DISCLOSURE

Ideally, an OSA stimulator should begin stimulation immediately before the start of inspiration, continue stimulation throughout inspiration, and stop stimulation at the end of the inspiration. Continual stimulation can result in therapeutic fatigue, decreased efficacy, and a shorter recharge interval. The present disclosure addresses these and other shortcomings by providing systems and methods that can accurately detect inspiration and/or expiration using auscultation data collected using an acoustic sensor (e.g., an acoustic transducer or pressure sensor optimized to detect an acoustic signal) to pick up sounds within the body of a patient. The acoustic sensor can reside within the IPG, be placed within or in proximity to the electrode(s) used to stimulate an upper airway muscle or a lead connecting the IPG and the electrode(s), or it can reside in a separate wired or wireless device (e.g., an acoustic transducer provided as an external device configured to obtain sensory data when placed in contact with or in proximity to a subject's skin). The collected auscultation data can be used to accurately determine the start and/or end point of a subject's inspiration cycle, allowing for precise administration of stimulation. Moreover, such systems reduce surgical time by not requiring a second lead for placement of a pressure sensor (e.g., to detect movement of the subject's thoracic or abdominal cavity during respiration).

The following presents a simplified summary of one or more aspects in order to provide a basic understanding of such aspects. This summary is not intended as an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In a first general aspect, the disclosure provides a system for treating obstructive sleep apnea in a patient comprising: at least one acoustic sensor configured to detect a plurality of acoustic signals generated by the patient; and a stimulator comprising: a stimulation system configured to deliver stimulation to a nerve which innervates an upper airway muscle; and a controller coupled to the stimulation system, and to the at least one acoustic sensor; wherein the controller is configured to measure the respiratory cycle of the patient based on one or more of the detected plurality of acoustic signals, and to cause the stimulation system to stimulate the nerve based on the measured respiratory cycle. As used herein, the term "respiratory cycle" refers to the timing of inspiration and expiration and respiratory rate of a patient.

In some aspects, the acoustic sensor is a microphone. In some aspects, the acoustic sensor is a microphone configured to detect acoustic signals generated by the heart and/or lungs of the patient. In some aspects, the acoustic sensor is a pressure sensor optimized to detect acoustic signals. Additional devices that may be used as acoustic sensors include piezoelectric devices, microelectromechanical (MEMS) devices, strain gauges, and other sensors known in the art which can detect an acoustic signal generated by the heart and/or lungs.

In some aspects, the acoustic sensor is implanted in the patient and a) positioned within the chest wall of the patient, within an outer housing that contains the stimulation system or a portion thereof; or b) positioned at or in proximity to the distal end of a lead connecting the stimulation system to the nerve which innervates an upper airway muscle. In some aspects, the stimulation system is configured to deliver stimulation to the nerve which innervates an upper airway muscle using an array of electrodes, and the acoustic sensor is positioned within or in proximity to the array of electrodes. In others, the stimulation system is configured to deliver stimulation to the nerve which innervates an upper airway muscle using a lead connected to one or more electrodes, and the acoustic sensor is positioned within or in proximity to the lead. In some aspects, the system further comprises an internal sensor configured to generate a second signal corresponding to movement of the thoracic or abdominal cavity of the patient during respiration; and the controller is further coupled to the internal sensor and configured to measure the respiratory cycle of the patient based on the second signal.

In some aspects the system further comprises: a) at least one analog low pass filter ("LPF") or high pass filter ("HPF"); and/or b) at least one digital low pass filter or high pass filter. The at least one digital low pass filter or high pass filter may comprise software executed, e.g., by the controller. The low and high pass filters used by the systems and methods described herein may be configured to have a variety of different cut-off frequencies. For example, in some aspects the at least one low pass filter is configured to have a frequency cut-off of 2 Hz or lower (e.g., 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 Hz, or a cut-off within a range defined by any pair of these values). In some aspects, the at least one low pass filter is configured to have a frequency cut-off of 2 kHz or lower (e.g., 2.0, 1.9, 1.8, 1.7, 1.6, 1.5, 1.4, 1.3, 1.2, 1.1, 1.0, 0.9, 0.8, 0.7, 0.6 or 0.5 kHz, or a cut-off within a range defined by any pair of these values). In some aspects, the at least one high pass filter is configured to have a frequency cut-off of 50, 60, 70, 80, 90, 100, 110, 120, 130, 140, or 150 Hz, or a cut-off within a range defined by any pair of these values. In some aspects, the system comprises at least one bandpass filter configured to have high and low frequency cut-offs which match any of the frequency cut-offs used by the high and low pass filters described herein.

In some aspects, the system further comprises: a) at least one hardware-based low pass filter or high pass filter; and/or b) at least one digital low pass filter or high pass filter; wherein the controller is configured to cause the stimulation system to stimulate the nerve during the inspiratory portion of respiration; during the expiratory portion of respiration; or during the inspiratory portion and the expiratory portion of respiration. In some aspects, the controller is further configured to identify an inspiratory portion of the respiratory cycle of the subject after the detected plurality of acoustic signals have been processed using one or more signal processing operations (e.g., a Hilbert transform). Such operations may be analog, digital, or a combination thereof.

In a second general aspect, the disclosure provides systems for regulating a respiratory cycle of a patient, comprising: at least one acoustic sensor configured to detect a plurality of acoustic signals generated by the patient; and a stimulator comprising: a stimulation system configured to deliver stimulation to a nerve which innervates an upper airway muscle; and a controller coupled to the stimulation system, and to the at least one acoustic sensor; wherein the controller is configured to measure the respiratory cycle of the patient based on one or more of the detected plurality of acoustic signals, and to cause the stimulation system to stimulate the nerve based on the measured respiratory cycle. In some aspects, the acoustic sensor is a microphone capable of detecting acoustic signals generated by the heart and/or lungs of the patient. In some aspects, the acoustic sensor is implanted in the patient and a) positioned within the chest wall or neck of the patient, within an outer housing that contains the stimulation system or a portion thereof; b) positioned at or in proximity to the distal end of a lead connecting the stimulation system to the nerve which innervates an upper airway muscle; and/or c) positioned within or in proximity to a housing containing the stimulator.

In some aspects, the stimulation system is configured to deliver stimulation to the nerve which innervates an upper airway muscle using an array of electrodes, and the acoustic sensor is positioned within or in proximity to the array of electrodes. In some aspects, the stimulation system is configured to deliver stimulation to the nerve which innervates an upper airway muscle using a lead connected to one or more electrodes, and the acoustic sensor is positioned within or in proximity to the lead. In some aspects, the system further comprises an internal sensor configured to generate a second signal corresponding to movement of the thoracic or abdominal cavity of the patient during respiration; and the controller is further coupled to the internal sensor and configured to measure the respiratory cycle of the patient based on the second signal In some aspects, such systems further comprise at least one low pass filter, high pass filter or bandpass filter, which may each be: a) analog or digital; and b) implemented in hardware or software. In some aspects, the at least one low pass filter is configured to have a frequency cut-off of 2 Hz or lower (e.g., 1 Hz). In some aspects, the at least one high pass filter is configured to have a frequency cut-off of at least 50 Hz (e.g., 100 Hz). In some aspects, the at least one bandpass filter is configured to have a low frequency cut-off of 2 Hz or below, and a high frequency cut-off of at least 50 Hz (e.g., 100 Hz). In some aspects, the system further comprises a) at least one analog low pass filter or high pass filter; and/or b) at least one digital low pass filter or high pass filter; wherein the controller is configured to cause the stimulation system to stimulate the nerve during the inspiratory portion of respiration; during the expiratory portion of respiration; or during the inspiratory portion and the expiratory portion of respiration. In some aspects, the controller is further configured to identify an inspiratory portion of the respiratory cycle of the subject after the detected plurality of acoustic signals have been processed using one or more signal processing operations (e.g., a Hilbert transform).

In a third general aspect, the disclosure provides methods of treating sleep apnea using the systems described herein. It is understood that a method of treating sleep apnea may comprise any combination of the steps or parameters described herein. For example, in some aspects such methods may comprise acquiring sensory data from an acoustic sensor implanted in the subject, wherein the sensory data comprises acoustic signals generated by the heart and/or lungs of the patient; generating a filtered signal by filtering the sensory data using at least one low pass filter and at least one high pass filter; extracting a signal envelope from the filtered signal; extracting a respiratory waveform corresponding to a respiratory cycle of the patient, by applying a low pass filter to the extracted signal envelope; and stimulating a nerve innervating an upper airway muscle after detecting a stable respiratory cycle following an apneic event, wherein apneic events are determined based on the extracted respiratory waveform.

In some aspects, the signal envelope is extracted from the filtered signal using a Hilbert transform. In some aspects, the sensory data is filtered using a low pass filter and a high pass filter. In some aspects, the low pass filter is configured to reduce acoustic signals generated by snoring sounds produced by the patient, and the high pass filter is configured to reduce acoustic signals generated by the patient's heart. In some aspects, the low pass filter used to extract the respiratory waveform has a frequency cut-off of 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 Hz, or a cut-off within a range defined by any pair of these values). In some aspects, the at least one low pass filter used to generate the filtered signal has a frequency cut-off of 2 kHz or lower (e.g., 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 kHz, or a cut-off within a range defined by any pair of these values). In some aspects, the at least one high pass filter used to generate the filtered signal has a frequency cut-off of 50, 60, 70, 80, 90, 100, 110, 120, 130, 140, or 150 Hz, or a cut-off within a range defined by any pair of these values. In some aspects, at least one bandpass filter may be used to extract the respiratory waveform. The bandpass filter may be configured to have high and low frequency cut-offs which match any of the frequency cut-offs used by the high and low pass filters described herein (e.g., any combination of the values described in this passage).

In some aspects, the methods described herein may further comprise a step of acquiring a second set of sensory data from an implanted sensor corresponding to movement of the thoracic or abdominal cavity of the patient during respiration; and apneic events may be determined based on the extracted respiratory waveform and the second set of sensory data.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

FIG. 4A shows a LPF with $f_c$=1 kHz, and FIG. 4B shows a high pass filter with HPF with $f_c$=100 Hz.

DETAILED DESCRIPTION

Figure 1:
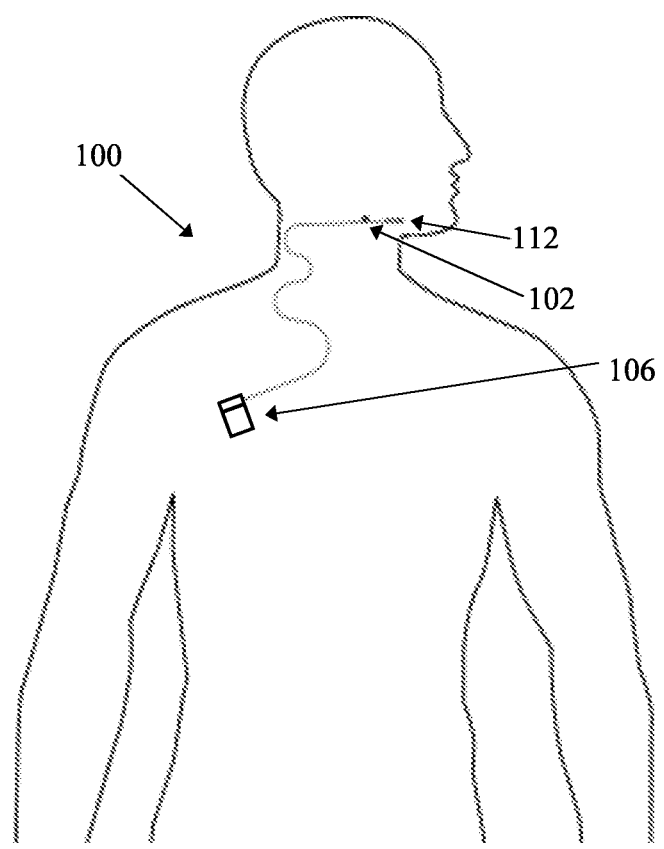
FIG. 1 is a diagram illustrating an exemplary embodiment of a system for treating obstructive sleep apnea.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various apparatuses and methods. These apparatus and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

FIG. 1 is a diagram illustrating an embodiment of a system 100 for treating obstructive sleep apnea using at least one acoustic sensor 102. It is envisioned that the at least one acoustic sensor 102 may be configured to detect acoustic signals produced by the heart and/or lungs of the patient. In some aspects, the at least one acoustic sensor 102 may comprise an acoustic transducer (e.g., a microphone). The acoustic sensor 102 may be used to detect sounds within the body for the purpose of detecting inspiration and/or expiration.

In this example, the acoustic sensor 102 positioned within the lead connecting the stimulation system 106 (e.g., an IPG) to an electrode innervating an upper airway muscle. In this case, the acoustic sensor 102 is also positioned towards the distal end of the lead, within proximity to the electrode 112. In alternative aspects, the acoustic sensor 102 may instead be positioned within the electrode 112 (or within the array of electrodes, as used in some exemplary aspects described herein). It may be advantageous to include the acoustic sensor 102 within the housing surrounding either of these elements (i.e., within a lead or electrode) in order to simplify manufacturing of the systems described herein. However, in other embodiments, it may be desirable to implant the acoustic sensor 102 as a separate element in proximity to the lead or electrode 112 (e.g., within 1, 2, 3, 4, 5, 6, 7, 8, 9, or 10 cm of either element). In cases where the acoustic sensor 102 is implanted separately, it may be configured to communicate with the stimulator 110 by means of a wired connection (e.g., a lead connecting the acoustic sensor 102 to the stimulation system 106) or a wireless connection (e.g., using Bluetooth).

In this example, the stimulator 110 is configured to be implanted within a patient and is coupled to an electrode 112 (e.g., via an implantable lead). Although one electrode is shown in FIG. 1, in other embodiments a plurality of electrodes may be used (e.g., two bilateral electrodes or an array of electrodes). The electrode 112 may be configured to be implanted within the patient, positioned to stimulate nerves which innervate an upper airway muscle. In some embodiments, the nerve is the hypoglossal nerve. In some embodiments which include two bilateral electrodes, each electrode may be configured to be implanted within the patient and positioned to stimulate a respective branch of the hypoglossal nerve (e.g., one electrode for the left branch, one electrode for the right branch). In some embodiments, the electrode 112 is a nerve cuff electrode.

Figure 2:
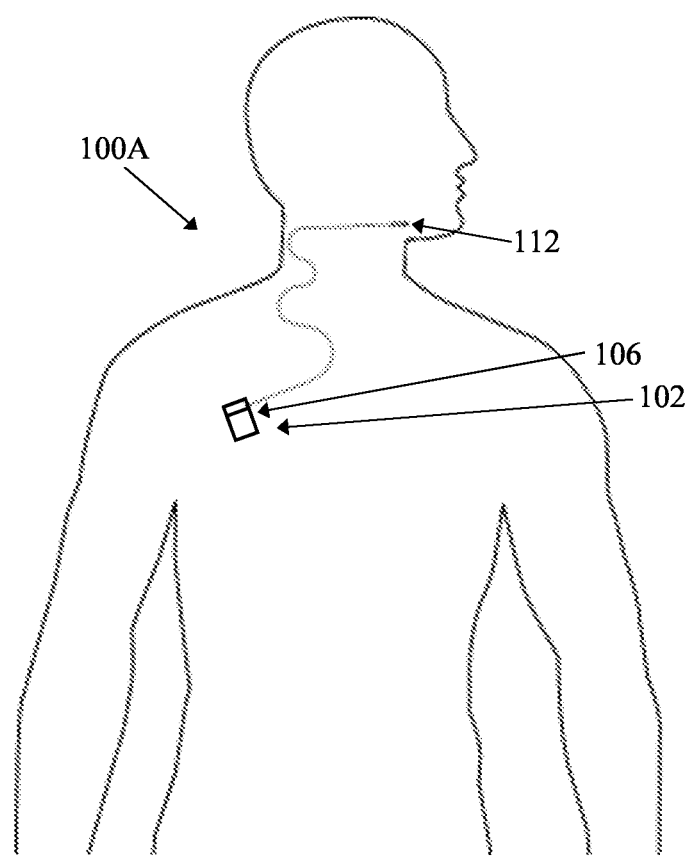
FIG. 2 is a diagram illustrating another exemplary embodiment of a system for treating obstructive sleep apnea.

FIG. 2 is a diagram illustrating an embodiment of a system 100A for treating obstructive sleep apnea using an acoustic sensor 102 positioned within the housing containing the stimulation system 106 (e.g., an IPG), rather than within a lead connecting the stimulation system 106 to an electrode 112 innervating an upper airway muscle, as in FIG. 1. The inclusion of an acoustic sensor 102 (e.g., an acoustic transducer such as a microphone) within the housing of an IPG may be advantageous in that it reduces the need for an additional surgical procedure to implant the acoustic sensor 102.

Figure 3:
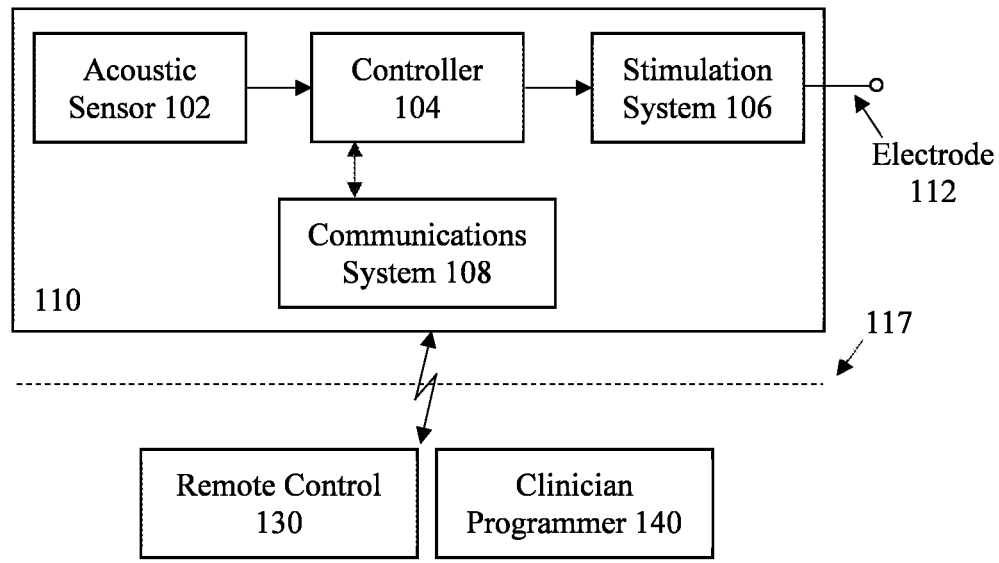
FIG. 3 is a block diagram illustrating an exemplary embodiment of a system for treating obstructive sleep apnea.

FIG. 3 is a block diagram of an exemplary embodiment of a system 100 for treating obstructive sleep apnea. It includes an implantable stimulator 110, a remote control 130, and a clinician programmer 140. In this example, the stimulator 110 includes an acoustic sensor 102, a controller 104, a stimulation system 106 (e.g., an IPG), an electrode 112, and a communications system 108.

The acoustic sensor 102 may be configured to detect and/or measure sensory data (e.g., acoustic signals) that can be processed to determine the respiratory cycle of the patient, and to transmit the sensory data to the controller 104. The stimulation system 106 (e.g., an implantable pulse generator, "IPG") may be configured to apply stimulation to the electrode 112. The controller 104 may be configured to control when and/or how the stimulation system 106 applies stimulation to the electrode 112. The controller 104 may be configured to determine the respiratory waveform of a human subject, or a model of the respiratory waveform based at least in part on the sensory data from the acoustic sensor 102, and to control the stimulation system 106 based on the respiratory waveform or model respiratory waveform. For example, the controller 104 may control the stimulation system 106 to apply stimulation during the inspiratory period of the respiration waveform, to apply stimulation during the expiratory period of the respiratory waveform, or to apply stimulation during particular parts of the inspiratory and/or expiratory portions of the respiratory waveform.

The communications system 108 may provide one or more wireless links 116, through the skin 117 of a subject, to the remote control 130, and/or the clinician programmer 140. The remote control 130, and the clinician programmer 140 may also include respective communications systems, which may provide wireless links 118 between the remote control 130, the clinician programmer 140, and/or additional Internet or cloud-based services. The wireless links 116 and/or 118 can utilize Bluetooth, Bluetooth Low Energy, or other wireless communication protocols. The wireless links 116 and/or 118 may include authentication and encryption suitable to protect patient data.

In some embodiments, the acoustic sensor 102 is an acoustic transducer (e.g., a microphone). The sensory data from the acoustic sensor 102 can be the primary source of data for the controller 104 to determine the appropriate stimulation timing or parameters to be given to the stimulation system 106 and to the nerve being stimulated via the electrode 112.

The system 100 may be configured to deliver stimulation to a nerve innervating the upper airway of the patient through the electrode 112 implanted proximate to the nerve. In some embodiments, the nerve is the hypoglossal nerve. In some embodiments, the upper airway muscle comprises the genioglossus, the geniohyoid, or some combination thereof. When the nerve is stimulated, it activates the upper airway muscle, thereby preventing or alleviating obstructive apneic events. In some embodiments, the stimulation system 106 applies stimulation to the nerve with an intensity sufficient to promote tonus in the upper airway muscle. In some embodiments, the stimulation system 106 applies stimulation to the nerve with an intensity sufficient to cause bulk muscle movement in the upper airway muscle. The stimulation system 106 is coupled to controller 104. The controller 104 receives the sensory data from one or more internal sensors 109 and/or from one or more acoustic sensors 102, and controls when the stimulation system 106 applies stimulation. In some embodiments, the controller 104 can control the intensity of the stimulation applied by the stimulation system 106. In some embodiments, the stimulation system 106 may apply different intensities of stimulation by changing the amplitude, the pulse width, or the frequency of the stimulation. In some aspects, the control 104 controls the amplitude, the pulse width, or the frequency of the stimulation applied by the stimulation system 106.

The stimulator 110 may be configured to receive sensory data from one or more acoustic sensors 102 (e.g., an acoustic sensor 102 positioned within or in proximity to a lead connecting the IPG to an electrode 112 or a housing containing the IPG) and to apply stimulation therapy to the patient based on the sensory data received from the acoustic sensor 102. The acoustic sensors 102 may be configured to collect data that can be used to monitor one or more physiological parameters of the patient, such as heart rate or respiration. Apneic events can be detected by determining that the regular respiratory pattern, as detected by the acoustic sensor 102 and/or an internal sensor 109, has become irregular for a number of cycles (e.g., at least 1, 2, 3, 4, 5, 6, 7, 8, 9, or 10 cycles). Waveforms and parameters indicative of an irregular respiratory pattern are disclosed, e.g., in U.S. Pat. Nos. 5,540,731 and 8,938,299, the entire contents of which are incorporated herein by reference. Data obtained from the one or more acoustic sensors 102 provides additional information that may be used by the controller 104 for apnea detection (e.g., heart rate rhythm and variability), providing potential benefits such as increased accuracy with respect to the administration of stimulation as a treatment for OSA.

In some aspects, the system 100 may use the sensory data generated by at least one acoustic sensor 102 to dynamically titrate therapy delivered to the patient, to determine when to apply stimulation to the patient, and/or when to turn stimulation therapy on or off. For example, the controller 104 may utilize heart rate data obtained by processing one or more signals from the acoustic sensor 102 to augment inertial data generated by an internal sensor 109, to make sleep stage decisions which may be more accurate than sleep stage decisions based on inertial data alone. In some embodiments, the controller 104 may use machine learning methods to make the sleep stage decisions. The controller 104 may control the stimulation applied by the stimulation system 106 based on the sleep stage decisions. For example, the controller 104 may utilize the sleep stage decisions to determine whether to turn stimulation therapy on and off (e.g., turning stimulation therapy on when the sleep stage decisions indicate that the patient is asleep, turning stimulation therapy off when the sleep stage decisions indicate that the patient is not asleep).

In some aspects, the system 100 may use the sensory data generated by at least one acoustic sensor 102 to determine parameters of the application of stimulation applied to the patient (e.g., where stimulation is applied during specific parts of the respiratory cycle, when to apply stimulation, and/or intensity of stimulation applied). For example, signals obtained from the acoustic sensor 102 may be processed to determine the respiratory cycle of the patient. The controller 104 may utilize this data, in addition to or as an alternative to the sensory data from the internal sensor 109, to evaluate or measure the respiratory cycle and control when stimulation is applied to the nerve during the respiratory cycle.

In some aspects, the system 100 may use the sensory data generated by at least one acoustic sensor 102 to control when to turn therapy on or off. For example, in some embodiments, the acoustic sensor 102 may be configured to obtains signals which can be processed to determine sleep stage, in addition to signals useful for detecting apneic events. Such systems can therefore also be used to turn on therapy at night and/or to dynamically titrate therapy based on the apnea-hypopnea index (AHI), which is an indication of the severity of a person's sleep apnea.

The remote control 130 may communicate with the stimulator 110 to control aspects of the operation of the stimulator 110 based on user input received at the remote control 130. For example, the remote control 130 may be configured to receive a user input identifying a selected intensity for treatment. The remote control 130 may communicate the selected intensity to the stimulator 110 via the communications system 108, and the controller 104 may control the intensity of therapy applied based on the selected intensity. In another example, the remote control 130 may be configured to receive a user input selecting an on/off state for the system 100. The remote control 130 may communicate the selected on/off state to the stimulator 110 via the communications system 108, and the controller 104 may control whether therapy is applied by the stimulator 110 based on the selected on-off state. The clinician programmer 140 may be configured to receive user input (e.g., from a clinician configuring the stimulator 110) and to transmit the user input to the stimulator 110 via the communications system 108. The user input received from the clinician programmer 140 may be configuration information for operation of the stimulator 110 (e.g., identifying contacts of a multi-contact electrode to which stimulation should be applied; identifying an intensity of stimulation to be applied or a range of allowed intensities), and the controller 104, the stimulation system 106, or another element of the simulator 110 may operate based on the received configuration information. The remote control 130 and/or the clinician programmer 140 may be implemented using a smartphone, tablet, or other computing device configured with an application for communicating with the stimulator 110.

In some embodiments, the Internet and/or cloud services 150 may provide a history related to OSA treatment for the patient. For example, the stimulator 110 may transmit data related to therapy applied (e.g., duration of applied stimulation or intensity of applied stimulation) or related to efficacy of treatment (e.g., apnea-hypopnea index (AHI)) to the remote control 130 or to the clinician programmer 140, and the remote control 130 or the clinician programmer 140 may transmit the data to the Internet and/or cloud service 150 to be compiled. In some embodiments, the Internet and/or cloud services 150 may provide for remote monitoring of OSA treatment for the patient. For example, the data related to therapy applied or related to efficacy of treatment may be compiled and made accessible to a doctor or clinician providing OSA treatment for the patient. In some aspects, the stimulator 110 may transmit the data related to therapy applied or related to efficacy of treatment to the remote control 130, the remote control 130 may transmit the data to the Internet and/or cloud services 150, and the clinician programmer 140 may access and display the compiled data to assist the user of the clinician programmer 140 in the configuration of the stimulator 110. In some embodiments, the Internet and/or cloud services 150 may provide for remote updating of OSA treatment for the patient. For example, the clinician or doctor may make configuration changes via the Internet and/or cloud services 150, and the Internet and/or cloud services 150 may transmit the configuration changes to the stimulator 110 via the remote control 130 or the clinician programmer 140.

In some aspects, the system 100 may further comprise an external power source (e.g., a rechargeable or primary battery pack) configured to power the at least one acoustic sensor 102, an internal sensor 109, the stimulation system 106, and/or the communications system 108. Power may be provided to any implanted components of the system, by induction.

As described in further detail herein, the acoustic signals detected by the acoustic sensor 102 may need to be subject to data processing via one or more analog or digital filters (e.g., one or more low or high pass filters, arranged in series or in parallel) in order to generate useful information. For example, the acoustic sensor 102 will often pick up an acoustic signal from various sounds within the body, e.g., heartbeat and snoring sounds, that may need to be filtered out to selectively identify the soft and low-pitched sounds arising from inspiration and expiration. In some aspects, digital filters will be preferable. However, implementations that perform analog filtering may be simpler and will often be more energy efficient.

Figure 4:
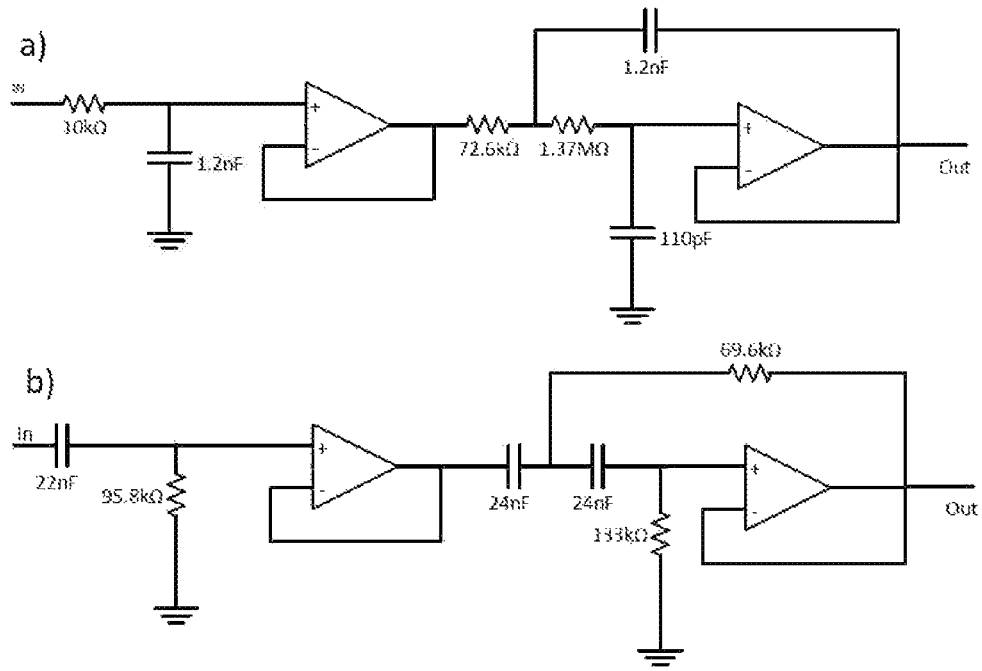
FIG. 4 is circuit diagram showing an exemplary $3^{rd}$ order (2 stage) Bessel filter with 60 dB/decade roll off. Specifically.

FIG. 4 shows an example of a hardware bandpass filter design which has demonstrated effective in the digital domain is shown. FIGS. 4A and 4B are low pass ($f_c$=1 kHz) and high pass (100 Hz) $3^{rd}$ order Bessel filters (2 stages), respectively, with a roll off of 60 dB/decade. The chosen low pass filter has a linear phase shift delay of 275 µs. However, other traditional filters may also be used.

Figure 5:
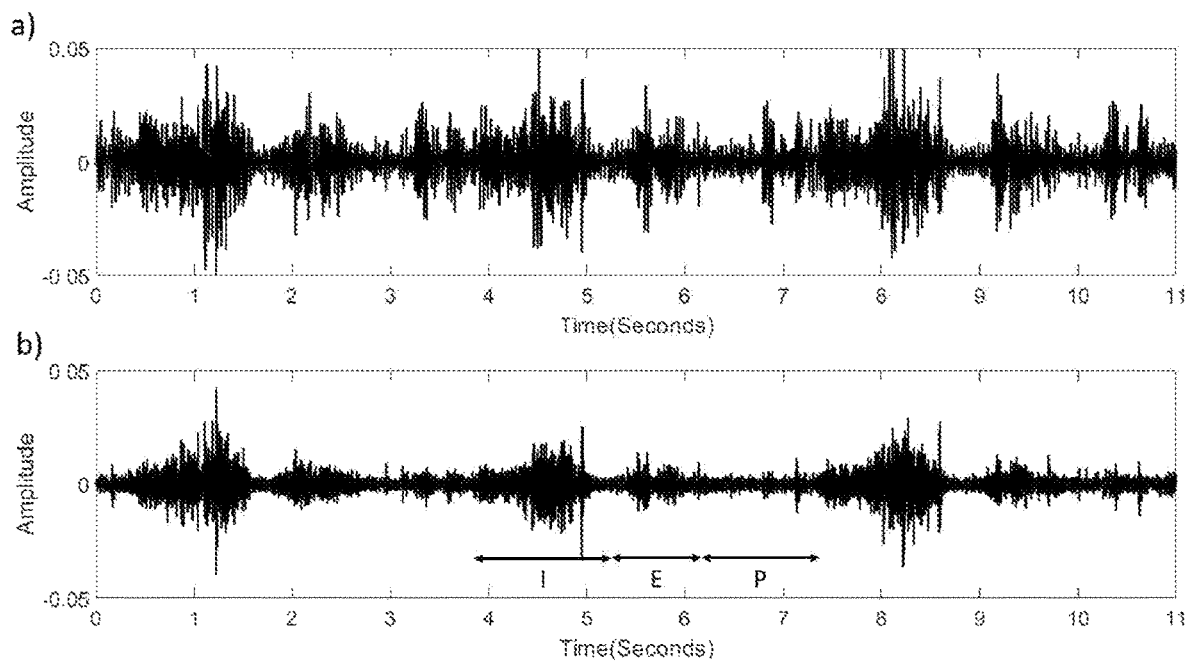
FIG. 5 is a pair waveform diagrams showing auscultation data recorded from over the lungs in raw (FIG. 5A) and filtered (FIG. 5B) form, using a filter in accordance with the circuit schematics provided in FIG. 4.

FIG. 5 illustrates the benefits of filtering the raw auscultation data obtained by the acoustic sensor 102. In this case, an example of an auscultated breath signal recorded from over the left lung was filtered using a $3^{rd}$ order (2 stage) Bessel filter in accordance with the circuit schematics provided in FIG. 4. The raw data is shown by the waveform provided in FIG. 5A, whereas the filtered waveform is provided in FIG. 5B. The filtered waveform plotted in FIG. 5B shows soft and low-pitched sound which is typically softer during expiration than inspiration when recording from over the lungs. An example of inspiration (I), expiration (E) and pause (P) period following expiration are annotated.

Figure 6:
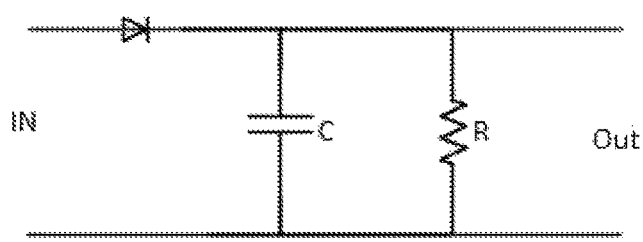
FIG. 6 is circuit diagram showing an analog implementation of a Hilbert transform.
Figure 7:
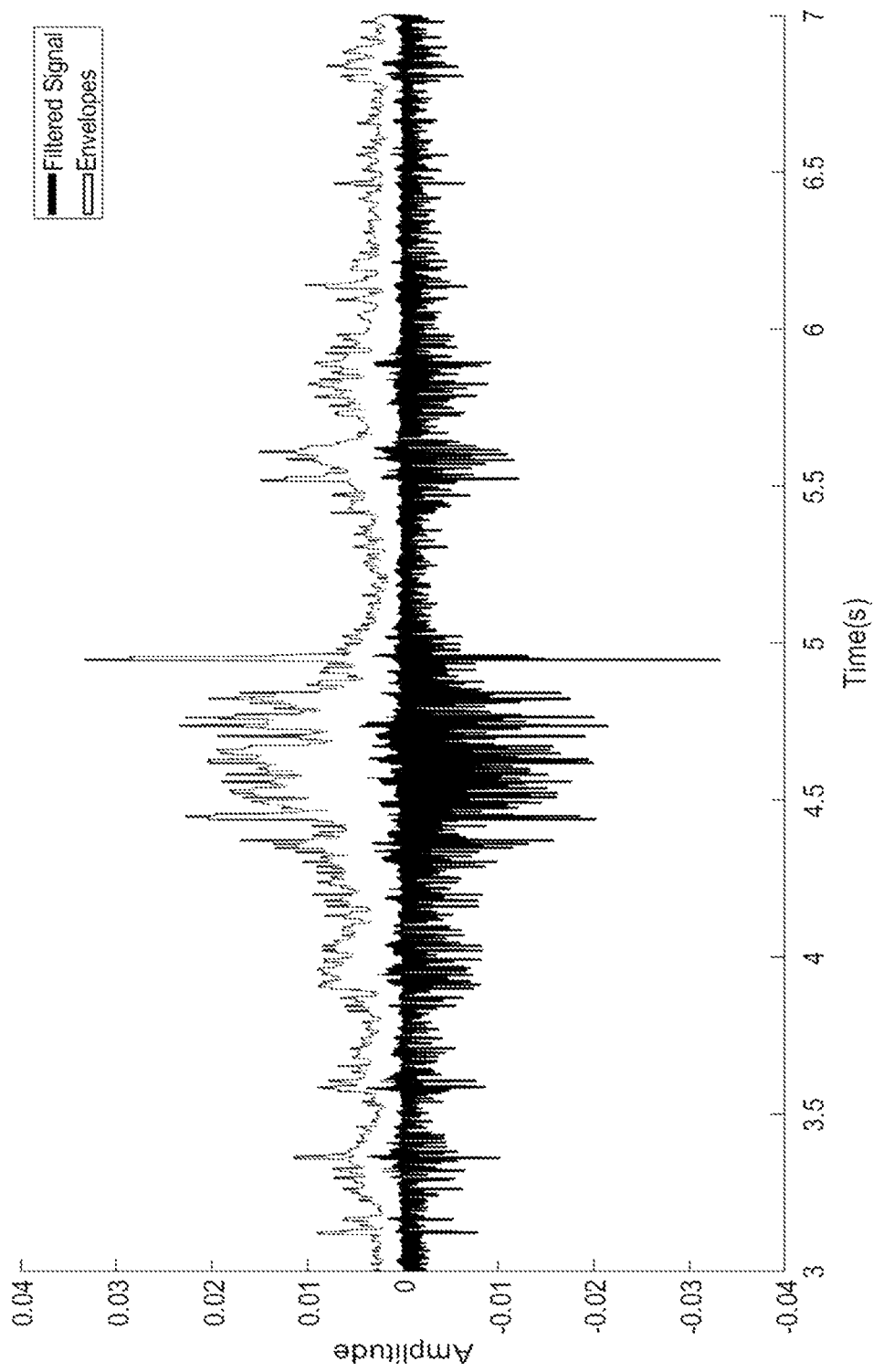
FIG. 7 is a waveform diagram showing an example of an enveloped audio signal produced by the filter shown in FIG. 6

Because the pitch of the inhalation sound is both broadband and patient-specific, one approach for signal extraction is to determine the envelope of the detected sound prior to extracting the desired signal. Although this can be done in software using techniques such as the Hilbert transform and Shannon energy envelope, in some aspects it may be simpler and more energy efficient to implement the envelope detector in hardware using, e.g., a diode, capacitor, and resistor as shown by the circuit diagram provided in FIG. 6. FIG. 7 shows an example of an enveloped audio signal produced by the filter shown in FIG. 6.

Figure 8:
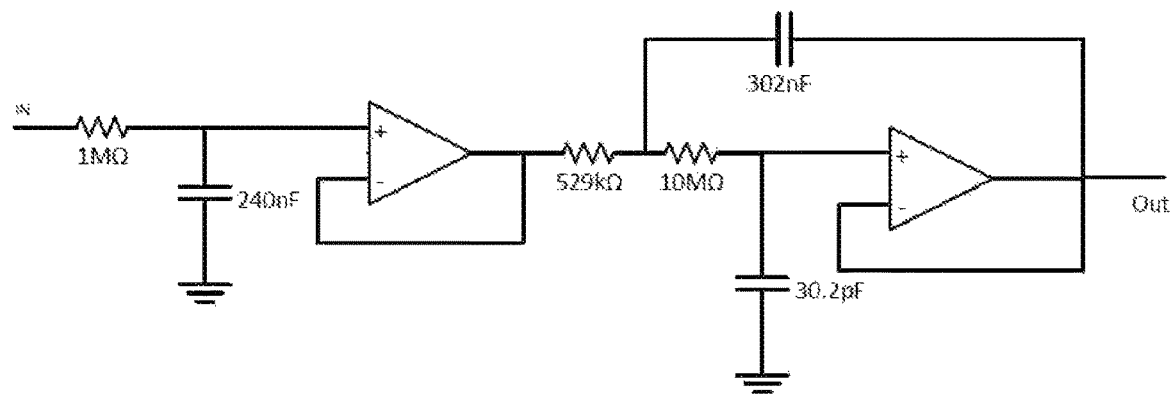
FIG. 8 is circuit diagram showing an exemplary hardware implementation of a low pass filter that can be used extract breathing activity from the signal envelope is shown in FIG. 7.

After determining the envelope of the detected sound (e.g., using a Hilbert transform), in some aspects it may be desirable to filter the sound signal to detect the start and end of inspiration. The frequency of breathing activity at rest for OSA patients is typically narrow-band and lies below 0.5 Hz. As with the previous steps, this filter may be implemented in hardware prior to digitization and peak detection. An exemplary hardware implementation of a low pass filter to extract breathing activity from the envelope is shown in FIG. 8, in the form of a low pass $3^{rd}$ order Bessel filter ($f_c$=0.5 Hz). This filter introduces a linear phase delay of 550 ms. However, other traditional filters may also be used. In some aspects, a low pass filter is selected for this step which has a frequency cut-off ($F_c$) of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 Hz, or an $f_c$ within a range defined by any pair of these values. In some aspects, a low pass filter is selected which generates a phase delay of 400 to 600 ms (e.g., 400, 410, 420, 430, 440, 450, 460, 470, 480, 490, 500, 510, 520, 530, 540, 550, 560, 570, 580, 590, or 600 ms, or a phase delay within a range defined by any pair of these values).

Figure 9:
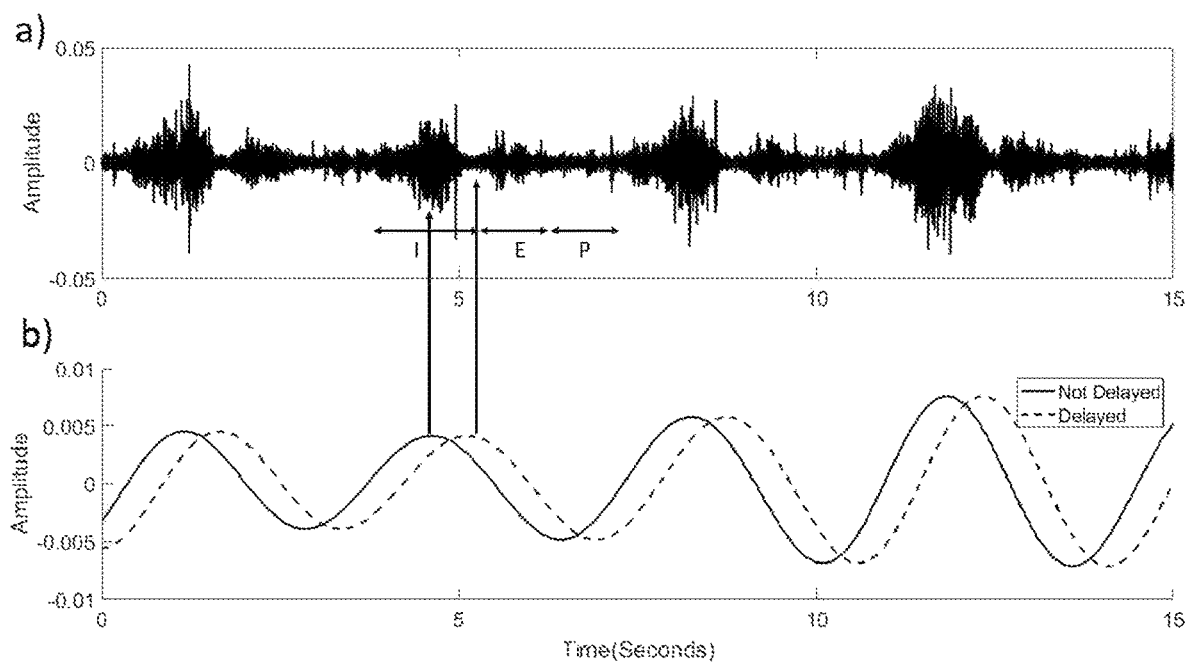
FIG. 9 is a pair of waveform diagrams showing breathing sounds of a patient (FIG. 9A) and processed using the low pass filter described in FIG. 8 (FIG. 9B).

Surprisingly, the phase delay introduced by this low pass filter is advantageous. FIG. 9A shows a waveform representing breathing sounds of a subject processed according to the preceding steps described above. This waveform was processed using the low pass filter described in FIG. 8, resulted in the waveform shown in FIG. 9B. As shown by FIG. 9B, the peak of the filtered signal without a phase delay does not correspond to end of inspiration (see FIG. 9B, solid trace). By extension, this also means that the trough of the filtered signal without a phase delay does not correspond to the start of inspiration. These discrepancies are due to the nature of the acoustic signal where the peak of the envelope is the high pitch region of inspiration, not the end of inspiration. The end of inspiration is the lowest point of the first envelope. However, the delay introduced by the low pass filter places the peak of the signal closer to the end of inspiration (see FIG. 9B, dashed trace).

Figure 10:
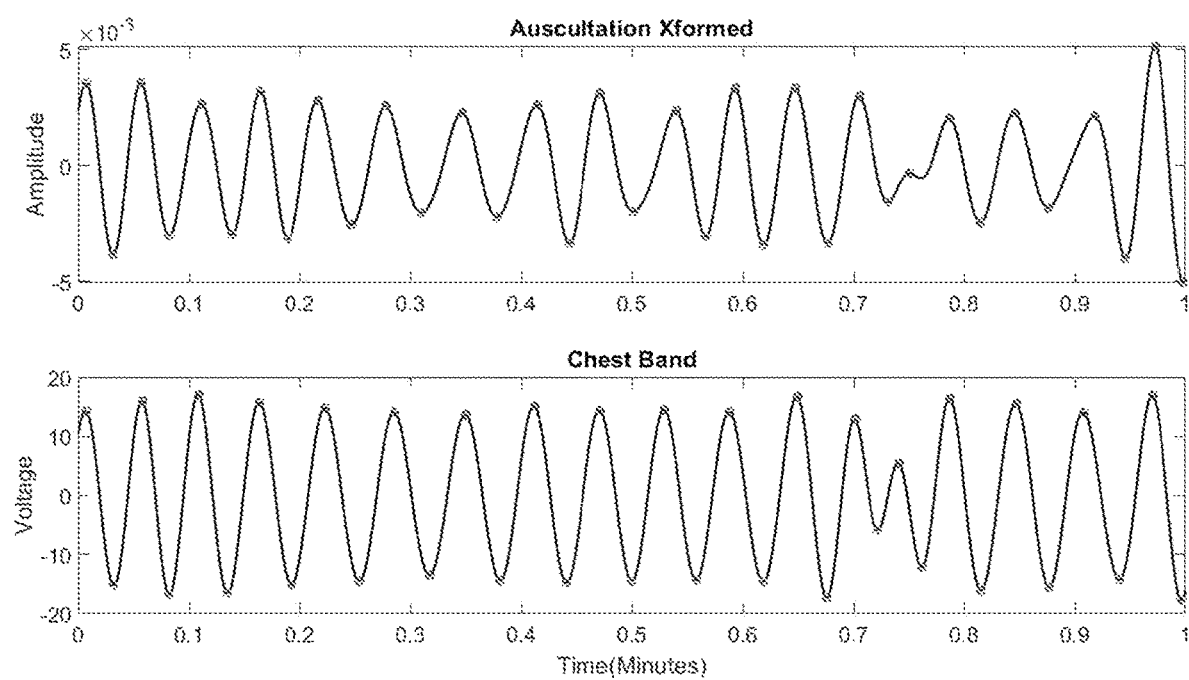
FIG. 10 is a pair of waveform diagrams showing a comparison of the filtered respiratory cycle waveform produced using the present methods (top) and a simultaneous reading generated by a RIP band as a control (bottom).

This filtered output can be used to identify the start and end of each respiration cycle, e.g., by locating the minimum and maximum points in the respiration signals, which correspond to the start and end points, respectively. FIG. 10 shows a pair of graphs which compare an auscultation waveform generated according to the present disclosure (top) and respiration data captured simultaneously using a RIP band (bottom). The RIP band method is an industry-recognized standard control for respiratory cycle studies. The peaks and troughs in this comparison are closely aligned, and these results validate the accuracy of the presently disclosed systems and methods.

Figure 11:
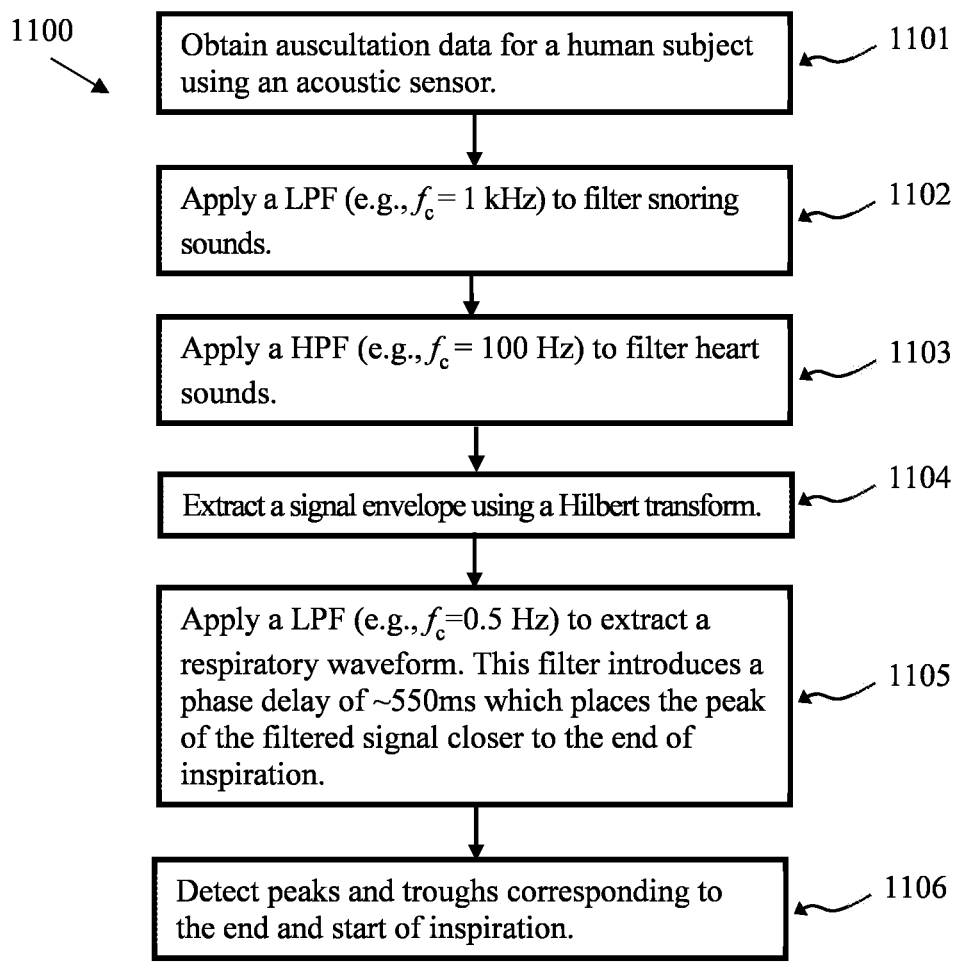
FIGS. 11-13 are flowchart diagrams illustrating exemplary methods for treating sleep apnea (e.g., using systems as described herein).
Figure 12:
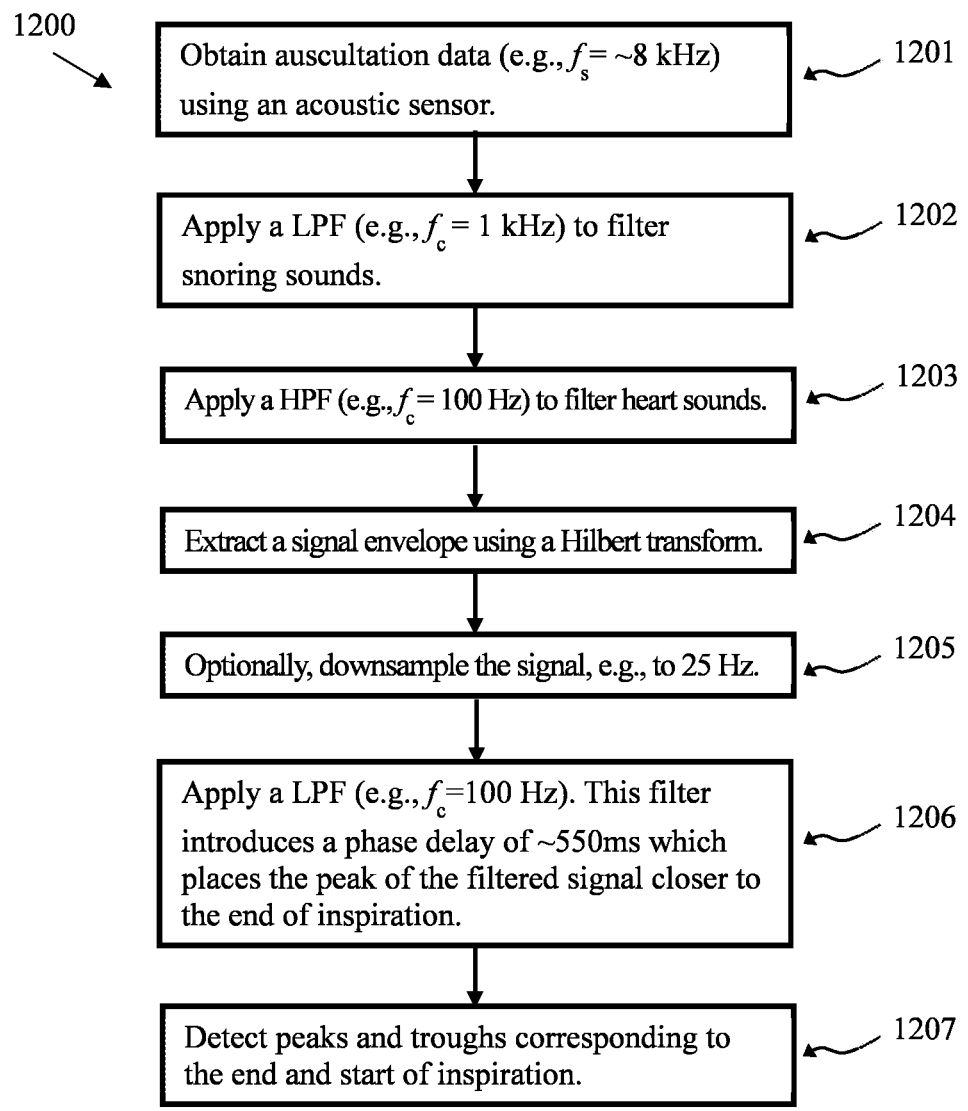
Figure 13:
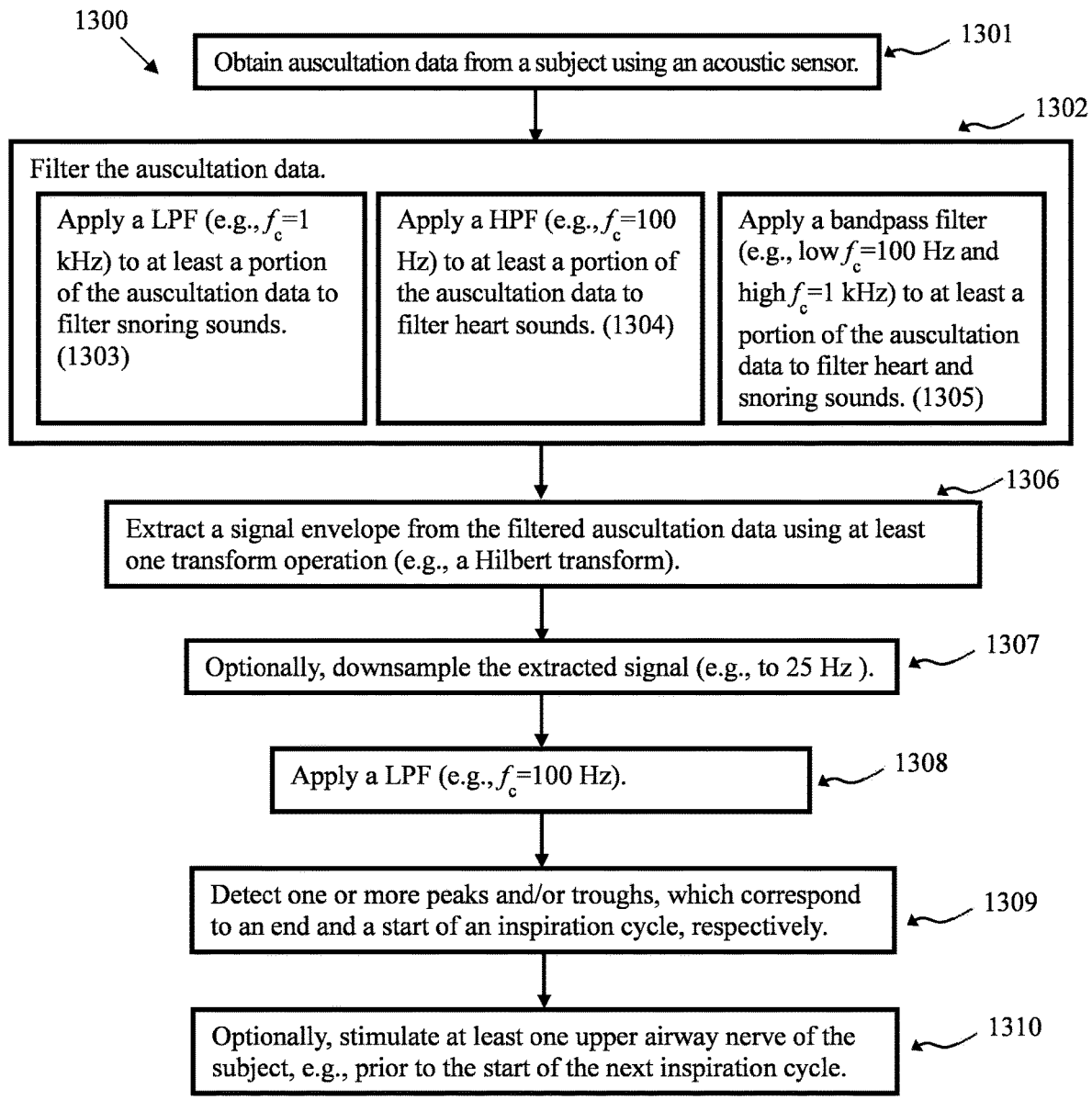

FIGS. 11-13 are flowchart diagrams illustrating exemplary methods for treating sleep apnea (e.g., using systems as described herein). FIG. 11 summarizes an exemplary method 1100 using an analog signal processing. Such methods may begin by obtaining auscultation data using at least one acoustic sensor described herein, e.g., a microphone or other audio transducer, at step 1101. This auscultation data may then be processed using a low pass filter and a high pass filter, as shown by steps 1102 and 1103. In this example, a low pass filter with a cut-off of 1 kHz and a high pass filter with a cut-off of 100 Hz were used. At step 1104, the filtered waveform is processed using a Hilbert transform to extract a signal envelope of the breathing sound signal obtained after applying the high and low pass filter in the previous steps. In the next step, a low pass filter is applied to the result (e.g., $f_c$=0.5 Hz). As explained above in the description related to FIG. 8, this low pass filter introduces a phase delay of ~550 ms which places the peak of the filtered signal closer to the end of inspiration. Finally, at step 1106, the peaks and troughs of the resulting signal can be used to identify the end and start of inspiration, respectively. Though not shown here in this exemplary flowchart, stimulation can be applied to the subject using this information regarding the respiratory cycle state, as described elsewhere herein. Moreover, it is understood that a bandpass filter (e.g., with similar or identical frequency cut-offs) may be used in place of the high and low pass filters used in this example.

FIG. 12 is directed to a similar implementation that uses digital signal processing, as opposed to analog methods. Such methods may begin, e.g., by obtaining auscultation data as in step 1201. Here, a sampling frequency (f) of approximately 8 kHz was used. At steps 1202 and 1203, low and high pass filters can be used, e.g., to filter out snoring and heart sounds, respectively. In this example, the same cut-off parameters are used as for the analog example discussed in the previous passage. Similarly, a Hilbert transform may be applied to extract a signal envelope of the breathing sound signal obtained after applying the high and low pass filter in the previous steps. At step 1205, a downsampling process may be applied to reduce the frequency (e.g., to 25 Hz as shown here). In alternative aspects, this step may be omitted and/or modified (e.g., by downsampling to a frequency of 10, 15, 20, 25, 30, 35, 40 Hz, or to a frequency within a range defined by any pair of these values). Finally, at step 1207, the peaks and troughs of the resulting signal can be used to identify the end and start of inspiration, respectively. Though not shown here in this exemplary flowchart, stimulation can be applied to the subject using this information regarding the respiratory cycle state, as described elsewhere herein. Again, as with the previous example, it is understood that a bandpass filter (e.g., with similar or identical frequency cut-offs) may be used in place of the high and low pass filters used in this exemplary method.

FIG. 13 is directed to another exemplary method 1300 for treating sleep apnea according to the disclosure. This example generalizes aspects of the methods shown in FIGS. 11 and 12. The method begins at step 1301 by obtaining auscultation data from a subject (e.g., using a system comprising at least one acoustic sensor 102 according to the present disclosure). This initial data is then filtered using one or more analog or digital filters at 1302. The filtering may be performed by a hardware-based filter (e.g., using a circuit as described herein) or a software-based filter (e.g., executed on the controller 104). It is contemplated that this filtering step will typically involve the use of high and low pass filters (e.g., as shown by steps 1303 and 1304) and/or at least one bandpass filter (e.g., as shown by step 1305) to filter out snoring and heart sounds detected by the acoustic sensor 102. In some embodiments, only one filter may be needed. In others, any combination of these filters may be applied to the auscultation data signal in series or in parallel, and may be applied to the whole signal or alternatively to one or more portions thereof. After filtering the signal, a signal envelope may be extracted from the filtered auscultation data signal using at least one transform operation (e.g., a Hilbert transform) at step 1306. The extracted signal envelope may then optionally be downsampled (e.g., to 25 Hz) at step 1307. A low pass filter (e.g., with a frequency cut-off of 100 Hz as used in the previous example) may then be applied at step 1308. As explained above, the use of a low pass filter at this point surprisingly improves the alignment between the peaks and troughs in the resulting signal and the end and start points of the inspiration cycle. It is understood that in some aspects, a frequency cut-off may be selected so as to result in a phase delay of approximately 400 to 600 ms (e.g., 400, 410, 420, 430, 440, 450, 460, 470, 480, 490, 500, 510, 520, 530, 540, 550, 560, 570, 580, 590, or 600 ms, or a phase delay within a range defined by any pair of these values). Next, at step 1309, the peaks and troughs of the resulting signal can be used to identify the end and start of inspiration, respectively. Finally, at step 1310, stimulation may be applied to at least one upper airway nerve of the subject. In this example, stimulation is applied prior to the start of the next inspiration cycle. It is understood that the data from the acoustic sensor 102 may be used as the primary determinant for selecting parameters for the stimulation (e.g., time and intensity parameters). In some aspects, the methods described herein may alternative utilize this respiration cycle data obtained from the acoustic sensor 102, plus additional physiological data obtained from one or more implanted sensors 109 (e.g., which may be configured to generate a signal corresponding to movement of the thoracic or abdominal cavity of the patient during respiration). In some aspects, the use of signal data from both sources may result in improved accuracy with respect to detection of the respiration cycle of the subject.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Terms such as "if," "when," and "while" should be interpreted to mean "under the condition that" rather than imply an immediate temporal relationship or reaction. That is, these phrases, e.g., "when," do not imply an immediate action in response to or during the occurrence of an action, but simply imply that if a condition is met then an action will occur, but without requiring a specific or immediate time constraint for the action to occur. The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed as a means plus function unless the element is expressly recited using the phrase "means for."

What is claimed is:

1. A system for treating a subject, comprising:
   at least one acoustic sensor configured to detect a plurality of acoustic signals generated by the subject;
   at least one inertial sensor configured to detect an inertial signal corresponding to a movement and/or an orientation of the subject; and
   a stimulator comprising:
   a stimulation system configured to deliver stimulation to a nerve which innervates an upper airway muscle; and
   a controller coupled to the stimulation system, to the at least one acoustic sensor, and to the at least one inertial sensor;
   wherein the controller is configured to
   determine a respiratory cycle of the subject based on one or more of the detected plurality of acoustic signals, wherein said determination comprises identifying an inspiratory portion of the respiratory cycle using one or more signal processing operations that introduce a linear phase delay of between 400 to 600 ms;
   determine whether the subject is asleep based on one or more of the detected plurality of acoustic signals and the inertial signal, and to
   cause the stimulation system to stimulate the nerve based on the determined respiratory cycle while the subject is asleep.

2. The system of claim 1, wherein the stimulation system is configured to treat obstructive sleep apnea.

3. The system of claim 1, wherein the acoustic sensor is a microphone capable of detecting acoustic signals generated by a heart and/or lungs of the subject.

4. The system of claim 1, wherein the acoustic sensor is implanted in the subject and
   a) positioned within a chest wall or neck of the subject, within an outer housing that contains the stimulation system or a portion thereof;
   b) positioned at or in proximity to a distal end of a lead connecting the stimulation system to the nerve which innervates an upper airway muscle; and/or
   c) positioned within or in proximity to a housing containing the stimulator.

5. The system of claim 1, wherein the stimulation system is configured to deliver stimulation to the nerve which innervates an upper airway muscle using an array of electrodes, and the acoustic sensor is positioned within or in proximity to the array of electrodes.

6. The system of claim 1, wherein the stimulation system is configured to deliver stimulation to the nerve which innervates the upper airway muscle using a lead connected to one or more electrodes, and the acoustic sensor is positioned within or in proximity to the lead.

7. The system of claim 1, wherein the system further comprises an internal sensor configured to generate a second signal corresponding to movement of a thoracic or abdominal cavity of the subject during respiration; and the controller is further coupled to the internal sensor and configured to measure the respiratory cycle of the subject based on the second signal.

8. The system of claim 1, further comprising at least one low pass filter, high pass filter or bandpass filter.

9. The system of claim 8, wherein the at least one low pass filter, high pass filter or bandpass filter is implemented in hardware or software.

10. The system of claim 1, further comprising at least one low pass filter configured to have a frequency cut-off of 0.5 Hz or lower.

11. The system of claim 1, further comprising at least one low pass filter configured to have a frequency cut-off of 2 kHz or lower.

12. The system of claim 1, further comprising at least one high pass filter configured to have a frequency cut-off of 100 Hz.

13. The system of claim 1, further comprising at least one bandpass filter configured to have a low frequency cut-off of 2 Hz or below, and a high frequency cut-off of 50 Hz or above.

14. The system of claim 1, further comprising:
a) at least one analog low pass filter or high pass filter; and/or
b) at least one digital low pass filter or high pass filter;
wherein the controller is configured to cause the stimulation system to stimulate the nerve during an inspiratory portion of respiration; during an expiratory portion of respiration; or during the inspiratory portion and the expiratory portion of respiration.

15. The system of claim 1, wherein the one or more signal processing operations comprise a Hilbert transform.

16. A method of treating obstructive sleep apnea in a subject comprising:
acquiring inertial data from an inertial sensor implanted in the subject, wherein the inertial data comprises one or more signals corresponding to a movement or an orientation of the subject;
acquiring sensory data from an acoustic sensor implanted in the subject, wherein the sensory data comprises acoustic signals generated by a heart and/or lungs of the subject;
generating a filtered signal by filtering the sensory data using at least one low pass filter and at least one high pass filter, or at least one bandpass filter;
extracting a signal envelope from the filtered signal;
extracting a respiratory waveform corresponding to a respiratory cycle of the subject, by applying a second low pass filter to the extracted signal envelope, wherein the second low pass filter comprises a filter that introduces a linear phase delay of between 400 to 600 ms;
determining whether the subject is asleep based on the inertial data and the extracted respiratory waveform; and
stimulating a nerve innervating an upper airway muscle of the subject, wherein stimulation is applied while the subject is asleep and after detecting at least one stable respiratory cycle following an apneic event, wherein apneic events are determined based on the extracted respiratory waveform.

17. The method of claim 16, wherein the signal envelope is extracted from the filtered signal using a Hilbert transform.

18. The method of claim 16, wherein the sensory data is filtered using a low pass filter and a high pass filter.

19. The method of claim 16, wherein the sensory data is filtered using at least one bandpass filter.

20. The method of claim 16, wherein the low pass filter is configured to reduce acoustic signals generated by snoring sounds produced by the subject, and the high pass filter is configured to reduce acoustic signals generated by the subject's heart.

21. The method of claim 16, wherein the low pass filter used to extract the respiratory waveform has a frequency cut-off of 0.1 to 1 Hz.

22. The method of claim 16, wherein the low pass filter used to extract the respiratory waveform has a frequency cut-off of 2 Hz or below.

23. The method of claim 16, wherein the bandpass filter is configured to have a low frequency cut-off of 2.0 Hz or below, and a high frequency cut-off of 50 Hz or above.

24. The method of claim 16, further comprising:
acquiring a second set of sensory data from an implanted sensor corresponding to movement of the thoracic or abdominal cavity of the subject during respiration; and
wherein apneic events are determined based on the extracted respiratory waveform and the second set of sensory data.

25. The system of claim 1, wherein the one or more signal processing operations comprise filtering using a low pass Bessel filter.

26. The method of claim 16, wherein the second low pass filter comprises a Bessel filter.

* * * * *